United States Patent
Chen et al.

(10) Patent No.: US 9,339,562 B2
(45) Date of Patent: May 17, 2016

(54) METHOD OF USING CT/MRI DUAL MODALITY CONTRAST AGENT

(75) Inventors: Chia-Chun Chen, Taipei (TW); Dar-Bin Shieh, Tainan (TW); Shang-Wei Chou, Ji An Township (TW); Ping-Ching Wu, Tainan (TW); Yu Hong Hsiao, Taichung (TW); Yu Sang Yang, Hsinchu (TW)

(73) Assignees: National Taiwan Normal University, Taipei (TW); National Cheng Kung University, Tainan (TW)

( * ) Notice: Subject to any disclaimer, the term of this patent is extended or adjusted under 35 U.S.C. 154(b) by 541 days.

(21) Appl. No.: 13/070,025

(22) Filed: Mar. 23, 2011

(65) Prior Publication Data

US 2012/0076737 A1 Mar. 29, 2012

(30) Foreign Application Priority Data

Sep. 28, 2010 (TW) .............................. 99132819 A

(51) Int. Cl.
*A61K 49/04* (2006.01)
*A61K 49/18* (2006.01)
*C22C 1/04* (2006.01)
*A61K 49/00* (2006.01)
*B22F 1/00* (2006.01)
*B22F 9/24* (2006.01)
*B82Y 5/00* (2011.01)
*B82Y 15/00* (2011.01)
*B82Y 30/00* (2011.01)

(52) U.S. Cl.
CPC ......... *A61K 49/0428* (2013.01); *A61K 49/0002* (2013.01); *A61K 49/1833* (2013.01); *B22F 1/0018* (2013.01); *B22F 9/24* (2013.01); *B82Y 5/00* (2013.01); *B82Y 15/00* (2013.01); *B82Y 30/00* (2013.01); *C22C 1/0466* (2013.01); *C22C 1/0491* (2013.01); *B22F 2001/0037* (2013.01)

(58) Field of Classification Search
None
See application file for complete search history.

(56) References Cited

U.S. PATENT DOCUMENTS 6,818,199 B1 * 11/2004 Hainfeld et al. ............. 424/1.11
2007/0269382 A1 * 11/2007 Santra et al. ................ 424/9.323
2008/0213189 A1 * 9/2008 Lee et al. .................... 424/9.32

FOREIGN PATENT DOCUMENTS

EP 1952919 A2 * 8/2008

OTHER PUBLICATIONS

Chou et al. In vitro and in vivo studies of FePt nanoparticles for dual modal CT/MRI molecular imaging. 2010 J. Am. Chem. Soc. 132: 13270-13278. Published online Jun. 24, 2010.*
Yano et al. Synthesis and characterization of magnetic FePt/Au core/shell nanoparticles. 2009 J. Phys. Chem. C 113: 13088-13091.*
Alric et al. Gadolinium chelate coated gold nanoparticles as contrast agents for both X-ray computed tomography and magnetic resonance imaging. 2008 J. Am. Chem. Soc. 130: 5908-5915.*
Woghiren et al. Protected thiol-polyethylene glycol: a new activated polymer for reversible protein modification. 1993 Bioconjug. Chem. 4: 314-318.*

* cited by examiner

*Primary Examiner* — Michael G Hartley
*Assistant Examiner* — Jennifer Lamberski
(74) *Attorney, Agent, or Firm* — Cesari and McKenna LLP

(57) ABSTRACT

Nanoparticles are used as a contrast agent for magnetic resonance imaging and computed tomography. Each of the nanoparticles includes a metal alloy core and a plurality of hydrophilic molecules covalently bound to the surface of the metal alloy core. Also disclosed is a method for using the contrast agent.

20 Claims, No Drawings

025 # METHOD OF USING CT/MRI DUAL MODALITY CONTRAST AGENT

CROSS REFERENCE TO RELATED APPLICATIONS

Pursuant to 35 USC §119(a), this application claims priority to Taiwanese Patent Application No. 99,132,819, filed Sep. 28, 2010. The content of the prior application is hereby incorporated by reference in its entirety.

BACKGROUND OF THE INVENTION

Computed tomography (CT) is a medical imaging tool that gives high-resolution 3D tomography information of anatomic structures based on different X-ray absorption of tissues and lesions. Iodinated compounds with high X-ray absorption coefficient have been used for CT contrast agents for decades. Recently, nanoparticle-based CT contrast agents (e.g., polymer-coated bismuth sulfide nanoparticles and PEG-coated gold nanoparticles) have been designed to provide better contrast effect than iodinated compound-based contrast agents.

Magnetic resonance imaging (MRI), on the other hand, provides unsurpassed 3D soft tissue details and functional information of lesions. Due to its non-ionizing radiation, high sensitivity to distribution of water and other biomolecules, MRI has been applied in clinic for diagnosis of many diseases. Gadolinium ($Gd^{3+}$)-based T1 contrast agents and superparamagnetic iron oxide nanoparticle-based T2 contrast agents are two major types of MRI contrast agents.

Only a few contrast agents with dual imaging contrast effect have been developed, e.g., Gd-G8 dendrimer and Gd chelated gold nanoparticles. See C. A. S. Regino, et al., *Contrast Media & Molecular Imaging*, 2008, 3, 2-8, C. Alric, et al., *J. Am. Chem. Soc.*, 2008, 130, 5908-5915. There is a need to develop new contrast agents that can be used in both CT and MR imaging.

SUMMARY OF THE INVENTION

One aspect of this invention relates to a method of imaging a subject. This method includes three steps: (1) administering to a subject an effective amount of a contrast agent, (2) scanning the subject by a magnetic resonance device or an X-ray computed tomography device, and (3) generating a magnetic resonance image or a computed tomography image of the subject from the scanning.

The contrast agent contains nanoparticles and an aqueous solvent in which the nanoparticles are dispersed.

The nanoparticles each include a metal alloy core and a plurality of hydrophilic molecules covalently bound to the surface of the metal alloy core.

The metal alloy core has an average diameter of 1-25 nm and is composed of a first metal (e.g., Pt, Pd, Au, and Ag) and a second metal (e.g., Fe, Co, Ni, and Mn). The first metal has an X-ray absorption coefficient of 6-11 $cm^2/g$ at 50 kiloelectron volt and the second metal is paramagnetic.

Each of the hydrophilic molecules can contain a sulfhydryl group and further contain a targeting moiety (e.g., an antibody).

Note that the contrast agent described above can be used as a dual modality contrast agent for both CT and MR imaging.

The details of several embodiments of the invention are set forth in the description below. Other features or advantages of the present invention will be apparent from the following actual examples and also from the appended claims.

DETAILED DESCRIPTION OF THE INVENTION

This invention is based on an unexpected discovery that certain nanoparticles can be used as compositions of a contrast agent for CT and MR imaging. More specifically, each nanoparticle includes a metal alloy core and a plurality of hydrophilic molecules.

"The metal alloy core contains two metals. The first metal has a high X-ray absorption coefficient (e.g., 6-11 $cm^2/g$ at 50 kiloelectron volt) so that the nanoparticles can provide contrast effects in CT imaging. Examples include Pt, Pd, Au, and Ag. The second metal has a paramagnetic property that can respond to an external magnetic field. Examples include Fe, Co, Ni, and Mn."

An adequate number of hydrophilic molecules are covalently bound to the surface of the metal alloy core so that the nanoparticles are distributed in water without precipitation. In one embodiment, the hydrophilic molecules each contain a sulfhydryl group. Examples include cysteamine, cystamine, and other mercaptoalkylamine. If desired, each of the hydrophilic molecules can also contain a targeting moiety that enables the nanoparticles to bind to a specific biological target (e.g., a tumor cell). Examples include an antibody, a peptide, an aptamer, a lectin, and a carbohydrate.

The above-described nanoparticles can be synthesized following the procedure described in S. W. Chou, et al., *J. Am. Chem. Soc.*, 2010, 132, 13270-78. Also, see actual examples below.

The nanoparticles thus obtained are dispersed in an aqueous solvent to form a contrast agent. The aqueous solvent must be compatible with the nanoparticles and not deleterious to subjects to be administered.

When used in CT or MR imaging, an effective amount of the contrast agent can be administered to a subject orally or intravenously. The term "an effective amount" refers to the amount of the contrast agent that is required to confer contrast effect on the subject. Effective amounts may vary, as recognized by those skilled in the art, depending on subject administered and the route of administration. The subject is then scanned by a magnetic resonance device or an X-ray computed tomography device. A magnetic resonance image or a computed tomography image of the subject is generated from the scanning.

Due to the high X-ray absorption coefficient and the paramagnetic property of the nanoparticles, the contrast agent can be applied in both MR and CT imaging.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Synthesis of Cysteamine-Capped FePt Nanoparticles and Anti-Her2 Antibody Tagged FePt Nanoparticles Platinum acetylacetonate ($Pt(acac)_2$, 97%) and dioctyl ether (90%) were purchased from Acros Organics, iron pentacarbonyl ($Fe(CO)_5$, 99.99%),1,2-hexadecanediol (90%), oleyl amine (70%), oleic acid (90%) and cysteamine (95%) were purchased from Sigma-Aldrich.

A. Synthesis of 2~4 nm FePt Metal Core $Pt(acac)_2$ (97 mg), 1,2-hexadecandiol (195 mg) and dioctyl ether (10 mL) were mixed and heated to 100° C. under $N_2$ for 10 min. $Fe(CO)_5$ (66 µL), oleyl amine (80 µL), and oleic acid (80 μL) were added to the mixture at 100° C. The reaction mixture was heated to 297° C. After 30 min, the heating source was removed and the product was cooled to room temperature. The product was precipitated by adding ethanol and separated by centrifugation.

The measurement of transmission electron microscopy (TEM) and energy-dispersive X-ray spectroscopy (EDX) was carried out on a Philips/FEI Tecnai 20 G2 S-Twin transmission electron microscope. A small amount of 2~4 nm FePt metal cores was dispersed in toluene. A drop of the dispersion fell on an amorphous carbon membrane supported by a copper grid. The FePt metal cores were determined at magnification of 50 k, 100 k, and 200 k.

TEM images showed that the sizes of FePt metal core were 3.58±0.34 nm. Their size distributions were obtained from average sizes of 100 metal cores and the results indicated that the FePt metal cores had narrow size distributions. Further, 2~4 nm FePt metal cores were in a spherical shape.

Powder X-ray diffraction (XRD) spectra were collected on a Bruker D8 Advance diffractometer. The FePt metal cores were placed on amorphous Si wafer and the workup procedure was carried out with Cu Ka radiation ($\lambda$=1.54178 Å). XRD spectra showed strongest peaks of (111) and (200) facets of a face-centered cubic (FCC) structure.

EDX analysis revealed that the alloying composition of the 2~4 nm FePt metal core was $Fe_{58}Pt_{42}$.

Magnetic measurements were performed by a superconducting quantum interference device (SQUID) magnetometer (MPMS, Quantum Design). The measurements were recorded between −10000 Oe and 10000 Oe at 300 K. The magnetic hysteresis loops indicated that the 2~4 nm FePt metal cores exhibited superparamagnetic behavior at 300K. The saturated mass magnetizations ($M_S$) at 300 K was 1.7 emu/g Fe. In addition, the effect of alloying component in mass magnetization was not obvious in the magnetic measurements.

B. Synthesis of 5~7 nm FePt Metal Core $Pt(acac)_2$ (97 mg), benzyl ether (4 mL), $Fe(CO)_5$ (66 μL), oleyl amine (100 μL), and oleic acid (100 μL) were mixed under $N_2$. The reaction mixture was heated to 240° C. at a heating rate of 15° C./min. After 30 min, the heating mantle was removed and then the product was cooled to room temperature. The particles were collected by centrifugation.

TEM images showed that the sizes of FePt metal cores obtained were 6.12±0.63 nm. Their size distributions were obtained from average sizes of 100 metal cores and the results indicated that the FePt metal cores had narrow size distributions. Further, 5~7 nm FePt metal cores were in a spherical shape.

XRD spectra showed strongest peaks of (111) and (200) facets of a face-centered cubic (FCC) structure.

EDX analysis revealed that the alloying composition of the 5~7 nm FePt metal cores was $Fe_{51}Pt_{49}$.

The magnetic hysteresis loops indicated that the 5~7 nm FePt metal cores exhibited superparamagnetic behavior at 300K. The saturated mass magnetizations ($M_S$) at 300 K was 3.2 emu/g Fe. In addition, the effect of alloying component in mass magnetization was not obvious in the magnetic measurements.

C. Synthesis of 11~15 nm FePt Metal Core

This experiment followed the procedure described in S. W. Chou, et al., *Chem. Mater.*, 2009, 21, 4955-4961. $Pt(acac)_2$ (195 mg), 1,2-hexacandiol (1.05 g), dioctyl ether (4 mL), $Fe(CO)_5$ (66 μL), oleyl amine (4 mL), and oleic acid (4 mL) were mixed under $N_2$ and then heated to 240° C. at a heating rate of 15° C./min. The mixture was kept at 240° C. for 60 min. Then the heating mantle was removed and the reaction mixture was cooled to room temperature. The final product was separated by addition of ethanol followed by centrifugation.

TEM images showed that the sizes of FePt nanoparticles obtained were 12.80±1.76 nm. Their size distributions were obtained from average sizes of 100 metal cores and the results indicated that the FePt metal cores had narrow size distributions. Further, 11~15 nm FePt metal cores were nearly in a cubic shape.

XRD spectra showed strongest peaks of (111) and (200) facets of a face-centered cubic (FCC) structure.

EDX analysis revealed that the alloying composition of the 11~15 nm FePt metal cores was $Fe_{33}Pt_{67}$.

The magnetic hysteresis loops indicated that the 11~15 nm FePt metal cores exhibited superparamagnetic behavior at 300K. The saturated mass magnetizations ($M_S$) at 300 K was 12.3 emu/g Fe. In addition, the effect of alloying component in mass magnetization was not obvious in the magnetic measurements.

D. Synthesis of Cysteamine-Capped FePt Nanoparticles

The 2~4 nm dry FePt metal cores (100 mg) were dispersed in ethanol by sonication. Cysteamine (~1 g) was added and dissolved into this dispersion at room temperature. The mixture was sonicated at 40~50° C. overnight and then washed by ethanol to remove cysteamine adsorbed on modified FePt nanoparticles. Finally, the cysteamine-capped 2-4 nm FePt nanoparticles were collected and stored in a bottle filled with $N_2$.

The cysteamine-capped 5~7 nm and 11~15 nm FePt nanoparticles were prepared following the same procedure as described above. They were also collected and stored in a bottle filled with $N_2$.

E. Synthesis of Anti-Her2 Antibody Tagged FePt Nanoparticles:

The cysteamine-capped 2~4 nm FePt nanoparticles were incubated with ethyl-3-[3-dimethylaminopropyl] carbodiimide hydrochloride and mouse anti-Her2 antibodies. The solution was stirred at 4° C. for 1 hr. The resultant FePt nanoparticles were centrifuged in 13000 rpm for 15 min and washed in phosphate-buffered saline (PBS) twice to yield 2~4 nm FePt-anti-Her2 nanoparticles.

The 5~7 nm and 11~15 nm FePt-anti-Her2 nanoparticles were obtained following the same procedure as described above.

Biocompatibility Test of Cysteamine-Capped FePt Nanoparticles

A. Cell Culture

Human oral epidermoid carcinoma cell line (OECM1) was maintained in RPMI-1640 medium supplemented with 10% (v/v) fetal bovine serum. Vero cells were maintained in DMEM medium containing 10% fetal bovine serum (FBS), 2 mM L-glutamine and 50 mg/mL gentamicin. The murine MBT-2 cell line derived from a carcinogen-induced bladder tumor in C3H/HeN mice was obtained from American type culture collection (ATCC, Manassas, Va.). Cells were maintained in DMEM supplemented with 10% FBS, 25 mM N-2-hydroxyethylpiperazine-N-2-ethanesulfonic acid (HEPES), 2 mM L-glutamine, and 1 mM sodium pyruvate. All the cell lines were maintained in a 37° C. incubator with a humidified environment of 5% $CO_2$ in the air. Medium was changed every two days.

B. In vitro Cytotoxicity Assay (MTT Assay)

In vitro cytotoxicity of FePt nanoparticles was evaluated in a Vero cell line by a MTT assay. A total of 5×10³ Vero cells/well were seeded in 96-well plates with DMEM supplemented with 10% FBS, 2 mM L-glutamine and 50 mg/mL gentamicin. After 24 hr, various sizes (2~4, 5~7, and 11~15 nm) and serial 10-fold dilutions of cysteamine-capped FePt nanoparticles were added to cells with final concentrations ranging from 0.01 to 100 mM (iron concentration) for additional 24 hr. Cell viability was detected using the 5-dimethylthiazol-2-yl-2,5-diphenyl tetrazolium bromide (MTT) assay. After the cells were treated with MTT and incubated at 37° C. for 4 hr, the purple formazan in supernatant was quantified by measuring 595 nm absorbance using a spectrophotometer.

The MTT assay results showed no significant cytotoxic response (cell viability >90%) detected at a concentration below 10 mM after 24 hr of exposure. Futher, at the highest concentration of 100 mM, cell viability was still up to 75%.

C. Hemolysis Assay

The hemolysis assay was performed using human whole blood from a healthy donor with informed consent following IRB guidelines. The water-dispersible cysteamine-capped FePt nanoparticles (2~4 nm, 5~7 nm, and 11~15 nm) were added to the 200 μL human whole blood stored in the Vacutainer (BD Inc., USA) containing 24 IU sodium heparin to the final concentrations in the range of 0.0001 to 100 mM (iron concentration). The tubes were gently mixed in a rotary shaker, and then incubated for 4 hr at 37° C. The specimens were then centrifuged under 1200 rpm for 10 min to collect the serum. The serum was further centrifuged under 13000 rpm for 15 min to remove the FePt nanoparticles and the supernatant was analyzed for the presence of the hemoglobin. More specifically, the free hemoglobin in the serum from lysed erythrocytes was detected by specific 545 nm spectrophotometric absorption to calculate the percentage of hemolysis upon exposure to various sizes and concentrations of FePt nanoparticles.

The results indicated that no significant hemolysis (<5%) occurred in all water-dispersible cysteamine-capped FePt nanoparticles at various concentrations.

Biodistribution Test of Cysteamine-Capped FePt Nanoparticles

Six-week old male C3H/HeN mice purchased from National Cheng Kung University Animal Center (Tainan, Taiwan) were anesthetized by 40 mg/Kg pantothol and were injected water-dispersible cysteamine-capped FePt nanoparticles (2~4 nm, 5~7 nm, and 11~15 nm) through tail vein at dose of 5 mg/kg for 12, 24, 48, 96,168 hr before sacrificed. After saline perfusion, organs such as the brain, heart, lung, spleen, liver, kidney, testis, and blood were collected and ground with nitro-hydrochloride acid. After filtration, the solution samples were analyzed by a flame atomic absorption spectrometer (UNICAM solar M6 series).

The results demonstrated that most of the FePt nanoparticles were cleared from major organs after 168 hr. All three sizes of FePt nanoparticles approached background levels after 96 hr. There were 102.2 μg/g of 11~15 nm FePt nanoparticles in the serum 48 hr after injection. By contrast, only 22.2 μg of 2~4 nm FePt nanoparticles and 49.6 μg/g of 5~7 nm FePt nanoparticles were detected at the same time point. The FePt nanoparticles were mainly accumulated in spleen followed by lung and liver and were gradually cleared from these organs with time. 11~15 nm FePt nanoparticles reached the plateau concentrations in these organs at 12 hr after injection, while it was 48 hr for 2~4 nm FePt and 5~7 nm FePt nanoparticles. The highest tissue concentrations of the nanoparticles in spleen and lung for 11~15 nm FePt were 241.5 μg/g and 120.4 μg/g, while they were 204.9 μg/g and 247.9 μg/g for 5~7 nm FePt. The plateau concentrations for 2~4 nm FePt nanoparticles were 146.6 μg/g in spleen and 96.5 μg/g in lung at 48 hr. 5~7 nm FePt nanoparticles demonstrated the lowest non-specific hepatic uptake. Transient accumulation of the FePt nanoparticles in brain in 24 hr for all three particle-sizes was also tested and 2~4 nm FePt nanoparticles had the highest brain concentration among them.

In vitro MR and CT Imaging

A. In vitro MR Imaging

Three arrays of Eppendorf tubes were prepared for MR imaging, which contained cysteamine-capped 2~4 nm FePt, 5~7 nm FePt, and 11~15 nm FePt nanoparticles with different concentrations (0.01~100 mM Fe in PBS) and PBS control. MRI was performed in a 1.5 T MR imager by the following sequences: $T_2$-weighted three dimensional fast-field echo sequences (repetition time in ms/echo time in ms/flip angle/number of acquisitions, 550/15/15°/3), field of view of 140×100 mm, a matrix of 256×196 pixels, and a slice thickness of 1.4 mm.

Significant dose dependent inverse MR imaging contrast was observed in all three arrays. The calculated intensity of each pellet was referred to that of PBS pellet and the normalized results were plotted. The 11~15 nm FeFPt array presented the most effective negative MR contrast and the signal intensity decreased by 86% at the low concentration of 10 mM Fe. The 2~4 nm FePt and 5~7 nm FePt arrays showed detectably image darkening by ~28% and ~33% at 25 mM Fe, respectively. Overall, 11~15 nm FePt exerted the best inverse contrast effect in the in vitro MRI experiment in a dose dependent manner.

B. In vitro CT Imaging

Three arrays of Eppendorf tubes were prepared for CT imaging, which contained cysteamine-capped 2~4 nm FePt, 5~7 nm FePt, and 11~15 nm FePt nanoparticles with different concentrations (0.01~100 mM Fe in PBS) and PBS control. CT data were acquired using a GE Light Speed VCT 64-detector CT. Imaging parameters were as follows: slice thickness, 0.625 mm; 120 kVp; 30 mA; field of view, 512×512; gantry rotation time, 0.4 s; table speed, 40 mm/rotation.

CT images demonstrated positive contrast enhancement in a dose dependent manner. Appreciable contrast enhancement for CT was observed at 1 mM Fe for all three sizes of nanoparticles. The CT signal value (about 100 HU) of 11~15 nm FePt at 100 mM Fe (corresponding to 44.7 mg FePt/mL) exhibited the equivalent ability of CT contrast as 48.4 mg/mL of the popular iodine-containing agent. See D. Kim, et al., *J. Am. Chem. Soc.*, 2007, 129, 7661-7665. In other words, the contrast effect of 11~15 nm FePt was about equal to that of the current iodine-containing agent at the same concentration. The CT signal value of 2~4 nm FePt was 83.3 HU at 100 mM Fe and the CT signal of 5~7 nm FePt was 88.2 HU at 100 mM Fe.

C. Selective in vitro Dual Modality Targeting Molecular Imaging of Her2/neu

A total of $10^7$ MBT2 and MBT2 with Her2 knock-down (MBT-KD) cells were fixed with 4% paraformaldehyde and resuspended into a 15 mL tube, then incubated with anti-Her2 antibody tagged FePt nanoparticles with average diameters of 2~4 nm and 11~15 nm and the control FePt nanoparticles (without tagged antibody) in a final iron concentration of 1 mM. After 4 hr incubation, $10^7$ cells in each group were placed in an Eppendorf tube array and analyzed for the contrast effect in a MR imager. The following pulse sequences were used: $T_2$-weighted sequence, fast spin echo with TR=550, TE=15,echo train length (ET)=10 ms. The array was then subject to CT scan following parameters described above in the in vitro CT imaging protocol.

For the molecular MR imaging, the signal intensities of FePt nanoparticles were normalized to the signal intensities of the background (MBT2 cells in PBS, MBT-KD cells in PBS). The results were as follows: for 2~4 nm FePt, the signal intensities of the cell pellets showed minor signal reduction (3.6%) in MBT-KD cells, while a 42% signal reduction was observed in MBT2 cells, which suggested that modulation of Her2/neu expression had an attributable effect to the non-specific uptake activity of 2~4 nm FePt. On the other hand, both MBT-KD and MBT2 cells showed about equal signal intensity reduction when they were targeted by 11~15 nm FePt (47.6% for MBT-KD cells and 49.7% for MBT2 cells), which suggested that non-specific uptake of 11~15 nm FePt was not significantly affected by the Her2/neu expression. By contrast, both 2~4 nm-FePt-anti-Her2 and 11~15 nm-FePt-anti-Her2 demonstrated significant Her2/neu expression dependent signal reductions. More specifically, drastic reductions in MRI signal intensities (73.7% for 2~4 nm-FePt-anti-Her2 and 65.0% for 11~15 nm-FePt-anti-Her2) were observed when comparing the MRI signals of the MBT2 cells to those of the MBT-KD cells. On the other hand, the appreciable differences in the targeting nanoparticles conjugated with anti-Her2 antibody demonstrated the selectivity for Her2/neu high expression cells. In particular, 11~15 nm-FePt-anti-Her2 exerted the best MR contrast due to their higher magnetic susceptibility.

For the molecular CT imaging, a significant effect of the particle size to the targeting contrast enhancement was observed. For 2~4 nm-FePt-anti-Her2 nanoparticles, a 3.3 times (3.3×) positive contrast enhancement was observed in MBT2 cells compared to MBT-KD cells. Yet, the overall CT signal intensity of 3 nm-FePt nanoparticles was low compared to that of 11~15 nm-FePt nanoparticles. CT contrast enhancement was observed in both MBT-KD (7.7×) and MBT2 (3.1×) targeted by 12 nm-FePt nanoparticles. 11~15 nm-FePt-anti-Her2 nanoparticles successfully differentiated MBT2 cells from MBT-KD cells where a 3.1× signal intensity enhancement was detected.

In vivo Targeting Molecular Imaging of CT and MR

The in vivo imaging was performed using mice with transplanted MBT2 tumor. The male C3H/HeN mice 6 to 8 weeks old were provided by National Cheng Kung University Laboratory Animal Center (Tainan, Taiwan). MBT-2 tumor lesions were established by subcutaneous dorsal flank injection of $10^7$ tumor cells in 100 μl normal saline using a 27-gauge needle. Visible tumor was normally observed one week after implantation. Animals were anesthetized using 2% isoflurane (Abbott Laboratories, Abbott Park, Ill.) mixed with 100% $O_2$ delivered using a veterinary anesthesia delivery system (ADS 1000; Engler Engineering Corp., Hialeah, Fla.). 11~15 nm-FePt (28 mM Fe concentration, 100 μL) conjugated to the anti-Her2 monoclonal antibody was injected into mice through tail vein (5 mg Fe/kg). The tumor lesions were then subject to the two imaging modality analysis. The images were taken at a time sequence from 0~24hrs using $T_2$-weighted MR acquisition sequence with the following parameters: fast spin echo with TR/TE=3000 ms/99.7 ms, ET=10 ms. The signal intensity of tissue in each test was determined by standard region-of-interest measurements of cross-sectional image of the tissue using the provided image quantification software. The in vivo micro-computed tomography analysis (Skyscan 1076 X-ray Microtomograph, Skyscan, Aartselaar, Belgium) was then performed using micro-focused x-ray source (50 keV/200 Ua) illumination; each image acquisition was performed when rotated 1 degree through 360 degrees. The images were processed for cross sections by reconstruction using NRecon (Skyscan) software.

Both MR and CT images were acquired before the injection and 24 hr after the injection. A significant 51% reduction of tumor lesion intensity in MR images was observed at 24 hr after injection. On the other hand, an unexpected 138% contrast enhancement of the tumor tissue was observed in CT images 24 hr after targeting.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of imaging a subject comprising:
   administering to a subject an effective amount of a contrast agent,
   scanning the subject with a magnetic resonance device and an X-ray computed tomography device, and
   generating a magnetic resonance image and a computed tomography image of the subject from the scanning,
   wherein the contrast agent contains (i) nanoparticles, each of which includes a metal alloy core and a plurality of hydrophilic molecules covalently bound to the metal alloy of the metal alloy core, the metal alloy core having an average diameter of 1-25 nm and composed of a metal alloy containing a first metal and a second metal, in which the first metal has an X-ray absorption coefficient of 6-11 $cm^2/g$ at 50 kilo-electron volt and the second metal is paramagnetic, and (ii) an aqueous solvent in which the nanoparticles are dispersed, wherein the nanoparticles are prepared by sonicating a mixture of the metal alloy core and the plurality of hydrophilic molecules.

2. The method of claim 1, wherein the first metal is selected from the group consisting of Pt, Pd, Au, and Ag; and the second metal is selected from the group consisting of Fe, Co, Ni, and Mn.

3. The method of claim 2, wherein the first metal is Pt and the second metal is Fe.

4. The method of claim 1, wherein each of the hydrophilic molecules contains a sulfhydryl group.

5. The method of claim 4, wherein the first metal is selected from the group consisting of Pt, Pd, Au, and Ag; and the second metal is selected from the group consisting of Fe, Co, Ni, and Mn.

6. The method of claim 1, wherein the first metal is Pt and the second metal is Fe.

7. The method of claim 4, wherein each of the hydrophilic molecules contains a targeting moiety.

8. The method of claim 7, wherein the first metal is Pt, the second metal is Fe, and the targeting moiety is an antibody.

9. The method of claim 1, wherein the metal alloy core has an average diameter of 2-4 nm; the first metal is selected from the group consisting of Pt, Pd, Au, and Ag; and the second metal is selected from the group consisting of Fe, Co, Ni, and Mn.

10. The method of claim 9, wherein each of the hydrophilic molecules contains a sulfhydryl group.

11. The method of claim 10, wherein each of the hydrophilic molecules further contains a targeting moiety that is an antibody.

12. The method of claim 11, wherein the first metal is Pt and the second metal is Fe.

13. The method of claim 1, wherein the metal alloy core has an average diameter of 5-7 nm; the first metal is selected from the group consisting of Pt, Pd, Au, and Ag; and the second metal is selected from the group consisting of Fe, Co, Ni, and Mn.

14. The method of claim 13, wherein each of the hydrophilic molecules contains a sulfhydryl group.

15. The method of claim 14, wherein each of the hydrophilic molecules further contains a targeting moiety that is an antibody.

16. The method of claim 15, wherein the first metal is Pt and the second metal is Fe.

17. The method of claim 1, wherein the metal alloy core has an average diameter of 11-15 nm; the first metal is selected from the group consisting of Pt, Pd, Au, and Ag; and the second metal is selected from the group consisting of Fe, Co, Ni, and Mn.

18. The method of claim 17, wherein each of the hydrophilic molecules contains a sulfhydryl group.

19. The method of claim 18, wherein each of the hydrophilic molecules further contains a targeting moiety that is an antibody.

20. The method of claim 19, wherein the first metal is Pt and the second metal is Fe.

\* \* \* \* \*